United States Patent [19]
Drent et al.

[11] Patent Number: 5,908,958
[45] Date of Patent: Jun. 1, 1999

[54] PROCESS FOR THE CARBONYLATION OF ACETYLENICALLY UNSATURATED COMPOUNDS

[75] Inventors: Eit Drent; Willem Wabe Jager, both of Amsterdam, Netherlands

[73] Assignee: Shell Oil Company, Houston, Tex.

[21] Appl. No.: 08/824,858

[22] Filed: Mar. 26, 1997

[30] Foreign Application Priority Data

Mar. 26, 1996 [EP] European Pat. Off. .............. 96200823

[51] Int. Cl.⁶ .................................................. C07C 67/36
[52] U.S. Cl. ............................................................ 560/207
[58] Field of Search ............................................. 560/207

[56] References Cited

FOREIGN PATENT DOCUMENTS

| | | |
|---|---|---|
| 0 186 228 A1 | 7/1986 | European Pat. Off. . |
| 0 271 144 A2 | 6/1988 | European Pat. Off. . |
| 0 386 833 A1 | 9/1990 | European Pat. Off. . |
| 0 386 834 A1 | 9/1990 | European Pat. Off. . |
| 0 441 446 A1 | 8/1991 | European Pat. Off. . |
| 0 565 199 A2 | 10/1993 | European Pat. Off. . |
| WO 95/05357 | 2/1995 | WIPO . |

OTHER PUBLICATIONS

J. Falbe's, "New Synthesis with Carbon Monoxide" (1980), p. 173.

*Primary Examiner*—Samuel Barts
*Assistant Examiner*—Rosalynd Keys

[57] ABSTRACT

The invention relates to a process for the carbonylation of acetylenically unsaturated compounds, whereby a feedstock comprising an acetylenically unsaturated compound and a relatively minor amount of an 1,2-alkadiene compound is contacted under carbonylation conditions with carbon monoxide and a co-reactant, in the presence of a catalyst system, based on: a) a source of cations of one or more metals of Group VIII of the Periodic Table; b) a phosphine having an aromatic substituent which contains an imino nitrogen atom separated by at least one bridging carbon atom from the phosphorus atom, and c) a protic acid, characterized in that the catalyst system is further based on d) a monodentate monophosphine or monophosphite.

10 Claims, No Drawings

PROCESS FOR THE CARBONYLATION OF ACETYLENICALLY UNSATURATED COMPOUNDS

FIELD OF THE INVENTION

The invention relates to a process for the carbonylation of acetylenically unsaturated compounds, whereby a feedstock of an acetylenically unsaturated compound and a relatively minor amount of an 1,2-alkadiene compound is contacted under carbonylation conditions with carbon monoxide and a co-reactant.

BACKGROUND TO THE INVENTION

In EP-A-0,271,144 a process is disclosed for the carbonylation of acetylenically unsaturated compounds in the presence of a catalyst system that can be formed from a palladium compound, a protic acid, and an organic monophosphine, e.g., diphenyl-2-pyridylphosphine.

A problem encountered with the processes for the carbonylation of acetylenically unsaturated compounds comprises poisoning of the catalyst by the isomeric 1,2-alkadiene compounds (so-called allenes) typically found therein. Small quantities of allenes, for example up to 0.4%, can often be tolerated, but the amounts commonly found in the acetylenic feed stocks present problems that need to be addressed before they can be used for the carbonylation process.

In EP-A-0,441,446 an improved carbonylation catalyst system is suggested that exhibits tolerance (e.g., up to 7%) under basic conditions, i.e., provided a tertiary amine is present (see comparative example G versus example 12). However, there is no suggestion in this reference that further improvements in respect of the carbonylation process, even carried out in the absence of the tertiary amine, could be achieved.

A further improvement in allene tolerance is disclosed in WO 95/05357. According to this document, the process should be conducted in the presence of a catalyst system based on a (di)phosphine having an aromatic substituent which contains an imino nitrogen atom and that is substituted with an electron-withdrawing group in a specified manner.

SUMMARY OF THE INVENTION

Surprisingly we now have found that at least as good allene tolerance with at least as good catalyst activity is achieved using a synergistic combination of ligands. Accordingly, a process is provided for the carbonylation of acetylenically unsaturated compounds, whereby a feedstock comprising an acetylenically unsaturated compound and a relatively minor amount of an 1,2-alkadiene compound is contacted under carbonylation conditions with carbon monoxide and a co-reactant, in the presence of a catalyst system, based on: a) a source of cations of one or more metals of Group VIII of the Periodic Table; b) a phosphine having an aromatic substituent which contains an imino nitrogen atom separated by at least one bridging carbon atom from the phosphorus atom, and c) a protic acid, characterized in that the catalyst system is further based on d) a monodentate monophosphine or monophosphite.

Due to the presence of the imino nitrogen atom, component b) is believed to act as a bidentate ligand, forming a chelate with the Group VIII metal cation. In particular when the imino nitrogen atom is separated by a single carbon atom, thus forming a four-ring chelate, good results are observed. The role of component d) is uncertain. It might form a complex with the Group VIII metal cation, but catalysts so prepared are of inferior catalytic activity. However, irrespective of its actual role, the fact remains that an impressive improvement has been observed.

DESCRIPTION OF A PREFERRED EMBODIMENT

Components a), b) and c) have been described extensively in the patent documents referred to above. Preferably, the Group VIII metal is a platinum group metal (Ni, Pd or Pt), most preferably Pd. Nonetheless, all of the Group VIII metals are known to provide Reppe catalysts that may find or have found use in the carbonylation of acetylenes, and are therefore within the scope of the present invention. The source of cations of metals of Group VIII is not important. Typically, it is provided as a metal salt, for instance of a carboxylic acid, or as a zero valent metal complex, or a complex of the metal in one of its oxidation states. Palladium acetate has proved to be a particularly suitable source of the preferred metal cation.

Similarly, component b) of the catalyst system has been described extensively and includes mono- and diphosphines having at least one heterocyclic ring containing an imino nitrogen atom represented by —N=which is separated from the phosphorus atom by one bridging carbon atom. This ring may bear further substituents. For example, component b) includes mono- and diphosphines containing a heterocyclic group selected from pyridyl, pyrazinyl, quinolyl, isoquinolyl, isoquinolyl, pyrimidinyl, pyridazinyl, cinnolinyl, triazinyl, quinoxalinyl and quinalolinyl. The groups wherein the imino nitrogen atom is separated by a single carbon atom from the phosphorus atom, i.e., selected from 2-pyridyl, 2-pyrazinyl, 2-quinolyl, 1-isoquinolyl, 3-isoquinolyl, 2-pyrimidinyl, 3-pyridazinyl, 3-cinnolinyl, 2-triazinyl, 2-quinoxalinyl and 2-quinalolinyl are preferred. Of those groups 2-pyridyl, 2-pyrimidyl and 2-triazinyl are particularly preferred.

Suitably, component b) is a monophosphine having one or two optionally substituted 2-pyridyl groups, the remaining group(s) being selected from optionally substituted phenyl groups and aLkyl groups, e.g., as disclosed in EP-A-0,386,834, incorporated herein by reference.

The function of the protic acid on which the catalyst system further is based (component c), is believed to provide a source of protons. The protic acid may be generated in situ.

Preferably the protic acid has a substantially non-coordinating anion, i.e. an anion which does not, or only to a very minor extent, coordinate with the metal of Group VIII. Preferred acids in this respect include acids having a pKa (at 18° C. in water) of less than 2, such as the so-called super acids; sulfuric acid; sulfonic acids; halogenated carboxylic acids; perhalic acids, such as perchloric acid, and acidic ion exchange resins, such as a sulphonated ion exchange resin. Hydrogen halides are preferably avoided since easily forming metal complexes and having a tendency to be corrosive. Preferred examples of suitable protic acids include optionally substituted aLkylsulphonic acids, such as sulphonic acid, (trifluoro)methanesulphonic acid, tert-butanesulphonic acid, and arylsulphonic acids such as toluenesulphonic acid.

Finally, component d) of the catalyst system may be an aromatic phosphine or phosphite, an aliphatic phosphine or phosphite, or a mixed aromatic/aliphatic phosphine or phosphite. The phosphine may be primary, secondary or, which is preferred, tertiary. The phosphite suitably is tertiary. Suitable phosphines and phosphites include those of the general formulae $PQ_3$ and $P(OQ)_3$, wherein each Q independently represents an optionally substituted aryl group, an optionally substituted (cyclo)alkyl group, or two or three Q's together form a ring wherein the phosphorus atom is the bridging group. Preferably, any aryl or alkyl group has up to 20 carbon atoms, whereas any cycloalkyl group has 5 to 7 carbon atoms in the ring. Most preferably, component d) is a phosphine, of which typical examples may be found in EP-A-0,186,228, incorporated herein by reference. Preferably triphenylphosphine is used, being relatively cheap and easily available, although substituted triphenylphosphines in view of their superior properties may also be used.

It is observed that catalysts based on a bidentate diphosphine and a monodentate monophosphine have already been exemplified in EP-A-0,186,228 for carbonylation of (pure) acetylenes. However, this disclosure gives no clue to the improved allene tolerance that has now been found.

The number of moles of components b) and d) and of moles of protic acid per mole atoms of metal of Group VIII may vary considerably. Recommended amounts for components b) and d) are each in the range of 10 to 200 moles per mole atom of metal of Group VIII and in particular in the range of 20 to 160. Suitably, the molar ratio of component d) versus component b) is in the range of 50:1 to 1:50, more suitably in the range of 20:1 to 1:20, subject to the concentration of allene in the feed. Thus, when a feed is used containing a relatively high amount of allene, then also a relatively high amount of component d) is employed. Preferred ratios will be easily recognized, as catalyst activity declines if more than optimal amounts of component d) are used. The amount of protic acid is preferably selected such that per mole atom of metal of Group VIII, 2 to 500 moles of protic acid are present.

The catalyst system of the invention may be homogeneous or heterogeneous, but is preferably homogeneous. The amount in which the catalyst is applied is suitably selected such that per mole of acetylenically unsaturated compound to be converted, from $10^{-8}$ to $10^{-1}$ mole atoms of Group VIII metal is present, preferably from $10^{-7}$ to $10^{-2}$ on the same basis.

Suitable acetylenically unsaturated compounds, to be used as starting material in the process of the invention, include optionally substituted alkynes with 2 to 20 carbon atoms per molecule. Examples are acetylene, propyne, 1-butyne, 2-butyne, 1-hexyne, phenyl acetylene and benzylethyne. Preferably, unsubstituted alkynes with 3 to 10 carbon atoms are used. In view of the industrial outlets for the carbonylated products, propyne is a preferred starting material.

As has been stated above, a major advantage of the catalyst systems of the invention consists in their tolerance towards 1,2-alkadiene compounds in the acetylenic feed stocks. Accordingly, commercially available feed stocks may be used that containing small amounts of 1,2-alkadiene compounds, such as propadiene, in addition to the acetylenically unsaturated compounds. In general, a 1,2-alkadiene content of at most 10%, based on acetylenically unsaturated compound, can be tolerated. It is recommended to use feed stocks in which the amount of 1,2-alkadiene compounds is lower, suitably in the range of 0.002 to 0.05 moles per mole of acetylenically unsaturated compound.

The co-reactant may be any hydroxyl-containing compound such as a monohydric, dihydric or polyhydric alkanol, a phenol, or water, but also comprises carboxylic acid, mercaptans and amines as disclosed in J. Falbe's "New Syntheses with Carbon Monoxide" (1980, page 173). Monohydric alkanols are preferred, in particular those having from 1 to 4 carbon atoms. Among these, methanol is most preferred.

The co-reactant is suitably used in excess, thereby avoiding the need of a separate diluent or solvent. However, a liquid diluent may be applied, if so desired. Preferably, non-alkaline diluents are used, such as ketones, e.g. methylisobutylketone, or ethers, e.g. dipropylether or 2,5,8-trioxanonane (diglyme).

Owing to the high activity of the catalysts, the process of the invention proceeds readily at moderate reaction conditions. Suitably the reaction may be carried out at ambient temperature, e.g., about 20° C., but the reaction temperatures will conveniently be in excess thereof, for instance in the range of 20 to 200° C., suitably in the range of 50 to 150° C. The reaction pressure is usually selected in the range of 1 to 100 bar. Pressures higher than 100 bar may be used, but are generally economically unattractive on account of special apparatus requirements. Preferably, the pressure is in the range of 5 to 70 bar.

The invention is illustrated with the following, non-limiting examples.

EXAMPLES

All experiments were carried out in a 250 ml "Hastelloy C" (trade mark) magnetically stirred autoclave. The autoclave was charged with 0.025 mmoles of palladium(II) acetate, the selected phosphines and methanesulphonic acid (MSA) or trifluoromethanesulphonic acid (TMSA) in the amounts indicated in the Table hereafter, and 50 ml of methanol.

Air was evacuated from the autoclave, whereupon 30 ml of a propadiene-containing propyne feed was added. Subsequently, carbon monoxide was supplied up to a pressure of 60 bar. The autoclave was sealed and heated to the desired reaction temperature.

As soon as the falling pressure remained constant (marking the completion of the reaction=rxn time), the contents of the autoclave were cooled and a sample was withdrawn and analyzed by gas liquid chromatography. The selectivities of the conversion of the propadiene-containing propyne feed and the mean conversion rates (based on mole product per mole Pd per hour) are listed in the Table.

As can be seen from Comparative Example A, a catalyst system based on a monodentate monophosphine has no tolerance with respect to propadiene. Comparative Example B teaches that the bidentate phosphine also lacks tolerance. Comparative Example C is example I(b) of WO 95/05357. Although performing fairly well, at slightly higher temperatures, as illustrated in Comparative Example D, the performances of these ligands deteriorate. This is unfortunate, as the reaction is exothermic and extensive cooling will be required if high performance is to be maintained. Comparative Example E is comparative example A(a) also of WO 95/05357. Comparative Example F is example 17 of EP-A-0,441,446, e.g., containing a tertiary amine rather than a monophosphine or monophosphite, and carried out with 30 ml of methanol and 30 ml MMA as solvent.

Example 1 to 3 illustrate that the combined presence of both components b) or d) does substantially increase the reaction rate, even in the presence of considerable amounts of propadiene. Examples 4 to 8 illustrate that the reaction rates may be further improved by substitution of either component b) or d).

TABLE

| Example | b)@ (mmole) | d)# (mmole) | c) (mmole) | allene (%) | T (C) | rxn time (hr) | rxn rate (mol/mol · hr) | sel. MMA (%) |
|---|---|---|---|---|---|---|---|---|
| A (comp) | — | PPh$_3$ (4) | MSA (4) | 3.0 | 60 | 5.0 | <10 | 89.0 |
| B (comp) | PN (1) | — | MSA (2) | 3.5 | 70 | 5.0 | 1.000 | 99.2 |
| C (comp) | 6-Cl—PN (1) | — | TMSA (2) | 2.2 | 45 | 0.5 | 24.000 | 99.6 |
| D (comp) | 6-Cl—PN (1) | — | TMSA (2) | 2.2 | 70 | 1.5 | 4.000 | 99.4 |
| E (comp) | PN (1) | — | TMSA | 2.3 | 50 | 5.0 | 625 | 99.0 |
| F (comp) | 6-Me—PN (1) | dimethyl-p-toluidine (10) | MSA (2) | 2.0 | 60 | 5.0 | 7.000 | 99.9 |
| 1 | PN (1) | PPh$_3$ (2) | MSA (2) | 3.1 | 70 | 0.5 | 30.000 | 99.0 |
| 2 | PN (0.5) | PPh$_3$ (3.5) | MSA (4) | 2.0 | 60 | 0.5 | 25.000 | 98.8 |
| 3 | PN (0.25) | PPh$_3$ (3.75) | MSA (4) | 2.8 | 60 | 1.0 | 7.000 | 99.2 |
| 4 | PN (1) | P(m-ClPh)$_3$ (3) | MSA (4) | 5.0 | 70 | 0.25 | 42.000 | 98.6 |
| 5 | PN (1) | P(p-MeOPh)$_3$ (3) | MSA (4) | 8.2* | 80 | 0.25 | 40.000 | 98.9 |
| 6 | 6-Cl—PN (1) | PPh$_3$ (3) | MSA (4) | 3.7 | 80 | 0.5 | 28.000 | 99.4 |
| 7 | 6-Bu—PN (1) | PPh$_3$ (3) | MSA (4) | 1.3 | 60 | 1.0 | 18.000 | 99.8 |
| 8 | 2,6-DPPN (0.25) | PPh$_3$ (3.75) | MSA (4) | 1.3 | 60 | 0.5 | 20.000 | 99.8 |

@PN = diphenyl-2-pyridylphosphine; 6-Cl—PN = diphenyl(6-cloro-2-pyridyl)phosphine; 6-Me—PN = diphenyl(6-methyl-2-pyridyl)phosphine; 6-Bu—PN = diphenyl(6-butyl-2-pyridyl)phosphine; 2,6-DPPN = 2,6-bis(diphenylphosphino)pyridine
PPh$_3$ = triphenylphosphine; P(m-ClPh)$_3$ = tri(meta-chlorophenyl)phosphine;
P(p-MeOPh)$_3$ = tri(para-methoxyphenyl)phosphine. Dimethyl-p-toluidine is not a component d) as defined in this specification.
*15 ml propyne/propadiene instead of 30 ml

We claim:

1. A process for the carbonylation of acetylenically unsaturated compounds, the process comprising the steps of:

providing a feedstock comprising an acetylenically unsaturated compound and a relatively minor amount of a 1,2-alkadiene compound;

contacting the feedstock under carbonylation conditions with carbon monoxide and a co-reactant, in the presence of a catalyst system based on: a) a source of cations of one or more metals of Group VIII of the Periodic Table; b) a phosphine having an aromatic substituent which contains an imino nitrogen atom separated by at least one bridging carbon atom from the phosphorus atom, c) a protic acid, and d) a component selected from the group consisting of monodentate monophosphine and monophosphite; and recovering a carbonylated product.

2. The process of claim 1, wherein the catalyst system comprises a monophosphine as component d).

3. The process of claim 1 wherein the catalyst system comprises a substituted or nonsubstituted triphenylphosphine as component d).

4. The process of claim 1 wherein the catalyst system comprises palladium as the Group VIII metal.

5. The process of claim 1 wherein the catalyst system comprises a mono- or diphosphine, each having an aromatic substituent which contains an imino nitrogen atom separated by a single bridging carbon atom from the phosphorus atom.

6. The process of claim 5 wherein the catalyst system comprises a substituted or nonsubstituted 2-pyridylphosphine as component b).

7. The process of claim 1 wherein the catalyst system comprises components b) and d) present in a molar ratio of 50:1 to 1:50.

8. The process of claim 1 wherein the amount of 1,2-alkadiene compound in the feedstock is less than 0.1 mole per mole of acetylenically unsaturated compound.

9. The process of claim 8 wherein the molar amount of 1,2-alkadiene compound in the feedstock per mole of acetylenically unsaturated compound is in the range of 0.002 to 0.05.

10. The process of claim 1 wherein methyl methacrylate is prepared by reacting a feedstock comprising propyne and 1,2-propadiene, with carbon monoxide and methanol.

* * * * *